US008582859B2

(12) United States Patent
Bakker

(10) Patent No.: US 8,582,859 B2
(45) Date of Patent: Nov. 12, 2013

(54) DETERMINING FORESHORTENING OPTIMAL VIEW MAPS TAKING INTO ACCOUNT THE SHAPE OF THE VESSEL CROSS-SECTION IN CARDIOVASCULAR X-RAY SYSTEMS

(75) Inventor: Nicolaas Hylke Bakker, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 363 days.

(21) Appl. No.: 13/057,512

(22) PCT Filed: Aug. 5, 2009

(86) PCT No.: PCT/IB2009/053396
§ 371 (c)(1),
(2), (4) Date: Feb. 4, 2011

(87) PCT Pub. No.: WO2010/018488
PCT Pub. Date: Feb. 18, 2010

(65) Prior Publication Data
US 2011/0135186 A1    Jun. 9, 2011

(30) Foreign Application Priority Data

Aug. 11, 2008  (EP) .................................. 08105006

(51) Int. Cl.
*G06K 9/00* (2006.01)
(52) U.S. Cl.
USPC ......................................................... 382/132
(58) Field of Classification Search
USPC ............ 382/128–132, 285; 434/272; 600/425
See application file for complete search history.

(56) References Cited

U.S. PATENT DOCUMENTS

| 6,047,080 | A  | 4/2000  | Chen et al. |
| 6,501,848 | B1 | 12/2002 | Carroll et al. |
| 7,289,841 | B2 | 10/2007 | Johnson et al. |
| 2004/0019264 | A1 | 1/2004 | Suurmond et al. |

FOREIGN PATENT DOCUMENTS

| WO | WO2008001260 | | 1/2008 |
| WO | WO 2008/001260 | * | 1/2008 |

OTHER PUBLICATIONS

Wink et al., "Intra-Procedural Coronary Intervention Planning Using Hybrid 3-Dimensional Reconstruction Techniques", Academic Radiology, vol. 10, No. 12, Dec. 2003, pp. 1433-1441.*
Kitslaar et al., "Automated Determination of Optimal Angiographic Viewing Angles for Coronary Artery Bifurcations from CTA Data", Prog. in Biomedical Optics & Imaging, 2008, Visualization, Image-Guided Procedures, and Modeling 2008, SPIE US, vol. 6918, Feb. 19, 2008, pp. 69181J-1-69181J-10.

(Continued)

*Primary Examiner* — Amara Abdi

(57) ABSTRACT

In clinical reality, the cross section of the lesions is frequently asymmetric. For clinical purposes it is crucial to find an X-ray view that gives a projection image where the minimum luminal cross section of the lesion is shown. In accordance with an exemplary embodiment of the invention, a system is proposed, wherein the system is adapted to perform the steps of a method of identifying modifications of an elongated element located in an object of interest. The method might comprise the steps of generating a plurality of projections of the object of interest, wherein the projections have different projection angles, determining geometrical aspects of the elongate element in each of the projections, calculating an index on the basis of the geometrical aspects, indicating projections having a desired value of the index.

10 Claims, 8 Drawing Sheets

(56) References Cited

OTHER PUBLICATIONS

Wink et al., "Intra-Procedural Coronary Intervention Planning Using Hybrid 3-Dimensional Reconstruciton Techniques", Academic Radiology, vol. 10, No. 12, Dec. 2003, pp. 1433-1441.

Masato et al., "Utility of Multisclice Computed Tomography as a Strategic Tool for Complex Percutaneous Coronary Intervention", the International Journal of cardiac Imaging, Kluwer Academic Publishers, DO, vol. 24, No. 2, Jun. 13, 2007, pp. 201-210.

* cited by examiner

DETERMINING FORESHORTENING OPTIMAL VIEW MAPS TAKING INTO ACCOUNT THE SHAPE OF THE VESSEL CROSS-SECTION IN CARDIOVASCULAR X-RAY SYSTEMS

FIELD OF THE INVENTION

The invention relates generally to a system and method for identifying modifications of an elongated element in an object of interest. Particularly, the invention relates to an asymmetry vessel lesion detection assistance.

BACKGROUND OF THE INVENTION

It is known in the art to visualize structures inside an object of interest by means of, for example, X-ray radiation. Such a visualization is available without the need of opening the object of interest, i.e. cutting or injuring or damaging or even destroying the object. Depending on the angle of radiation, the structures will be projected and, thus, seen only from one side.

Further known techniques provide the possibility of generating a 3D volume image of an object of interest, wherein, firstly, the object will be radiated from different point of views, i.e. different radiation angles, and, secondly, a 3D volume image is reconstructed on the basis of the different projections.

In the field of medical applications, angiography is used to detect a modification, i.e. a lesion or narrowing in a vascular bed by using a cardiovascular X-ray system to take images of the vessels during intra-arterial injection of a contrast material.

In order to get a proper assessment of a lesion, the orientation (rotation and angulation) of the X-ray system is critical.

Currently "Foreshortening Optimal Viewmaps" are used in cardiovascular X-ray systems and assist in determining the X-ray system orientation that will image the lesion with minimum foreshortening of the vessel length in the projection image. The optimal viewmap is based on 3D centerline geometry of the vessels that can be derived from e.g. 3D CT data or 3D Rotation Angiography data. The optimal viewmap is a map depicting average foreshortening of a selected vessel segment as a function of the X-ray system rotation and angulation. The Optimal Viewmap does not take the shape of the cross-section of the vessel into account.

In clinical reality, the cross section of the lesions is frequently asymmetric. For clinical purposes it is crucial to find an X-ray view that gives a projection image where the minimum luminal cross section of the lesion is shown. Depending on the X-ray view the diameter of the vessel in the projection image will appear differently for an asymmetric lesion. Finding the projection image with the minimum lesion diameter is crucial because treatment decision (to stent or not) are based on the procedural reduction in diameter as seen on the 2D projection image. For asymmetric lesions, depending on the X-ray view the diameter reduction may seem less severe than in reality leading to incorrect treatment decisions.

SUMMARY OF THE INVENTION

It might be an object of the invention to provide a method and a system for identifying modifications of an elongated element inside an object of interest, to assist the detection of special geometrical occurrence. It might be a further object of the invention to provide assistance in selection of optimal projections showing the geometrical aspects of interest in high resolution.

These might be achieved by the subject matter according to the independent claims. Further embodiments of the present invention are described in the respective dependent claims.

Generally and in accordance to an exemplary embodiment of the invention, a method of identifying modifications of an elongated element located in an object of interest, might comprise the steps of generating a plurality of projections of the object of interest, wherein the projections have different projection angles, determining geometrical aspects of the elongate element in each of the projections, calculating an index on the basis of the geometrical aspects, indicating projections having a desired value of the index.

By way of this method, it is possible to identify projections or several projections representing a region of the elongated element, in which region geometrical modifications of interest occur.

Generally, an elongated element might be a pipe, a tube, or a cylinder, arranged in an object, wherein the elongated element might have a hollow or a solid structure. Thus, a modification in the sense of the invention is any deformation of the cross section, i.e., the walls of the elongated element. In the case of an elongated hollow element or a tubular element, the deformation might be caused by deposition of for example calcium carbonate at the inner wall surface. In the case of the investigation of vessels in a body, these modifications might be lesions which deform the lumen of the vessel for example asymmetrically. Since the vessel will be usually filled with a contrast material during the investigation, the lumen of the vessel will have an appearance on an X-ray image like an elongated solid element. From this image, the deformations of the walls of the vessel might be reconstructed.

By way of numbering the successive projections it might be possible to provide information about the single projection or the group of projections showing an geometrical aspect of interest.

According to an aspect of the exemplary embodiment, the geometrical aspects might be a minimum diameter and a maximum diameter of the elongated element, measured perpendicular to the centre axis of the elongated element.

The diameter or the distance between two opposite walls of the elongated element might be easily determined in a projection image. Therefore, it might be possible to automatically determine the minimum and the maximum diameter of a elongated element in a view showing the cross section of that elongated element. The minimum and maximum diameter might serve to calculate an index representing the asymmetry of the cross section.

According to a further aspect of the exemplary embodiment, this asymmetry index might be normalized, so that the value of the asymmetry index is between 0 and 1 with higher values corresponding to more asymmetry and lower values corresponding to less asymmetry. This normalized asymmetry index might be calculated with the following formula.

$$(D_{max} - D_{min})/D_{max}$$

Additionally, the method according to the exemplary embodiment of the invention might further comprise the step of illustrating the elongated element together with a visualization of the value of the index relative to the corresponding region of the elongated element.

Beside providing only a number of a special projection, the projections with the geometrical aspect of interest might be indicated in a 2D or 3D image of the complete elongated element or at least a part or section of the elongated element.

According to another embodiment of the invention, a system for identifying modifications of an elongated element located in an object of interest, might comprise an imaging device, a processing device, and a calculation device. The imaging device might be adapted to generate a plurality of projections of the object of interest, wherein the projections have different projection angles. The processing device might be adapted to determine geometrical aspects of the elongate element in each of the projections, and might be further adapted to indicate projections having a desired value of the index. Finally, the calculation device might be adapted to calculate an index on the basis of the geometrical aspects.

It should be noted that the processing device and the calculation device might be implemented in a single computing unit. A computer program which is adapted to perform the method according to the invention, might be stored at a working memory of such a computing unit.

According to an aspect of the embodiment, the system might further comprise a display device illustrating the elongated element together with a visualization of the value of the index relative to the corresponding region of the elongated element.

Further, the system might be equipped with an input device like a keyboard or computer mouse to provide a user of the system with possibilities to interact with the system, i.e. to define the geometrical aspect of interest, or to choose the way of illustrating the index and/or the surrounding structures of the elongated element.

In other words, according to the invention and according to a special application in the medical field, a method is proposed that determines optimal X-ray views showing the highest procedural diameter reduction of a vessel lesion in the projection image by analyzing available 3D vessel data (from CT, 3D-Rotation Angiography or any other imaging modality) and taking into account the shape of the cross sectional area. An index of asymmetry is calculated and is displayed as a function of projection direction of the system.

The invention relates also to a computer program for a processing device, such that the method according to the invention might be executed on an appropriate system. The computer program is preferably loaded into a working memory of a data processor. The data processor is thus equipped to carry out the method of the invention. Further, the invention relates to a computer readable medium, such as a CD-Rom, at which the computer program may be stored. However, the computer program may also be presented over a network like the worldwide web and can be downloaded into the working memory of a data processor from such a network.

It has to be noted that embodiments of the invention are described with reference to different subject matters. In particular, some embodiments are described with reference to method type claims whereas other embodiments are described with reference to apparatus type claims. However, a person skilled in the art will gather from the above and the following description that, unless other notified, in addition to any combination of features belonging to one type of subject matter also any combination between features relating to different subject matters is considered to be disclosed with this application.

The aspects defined above and further aspects, features and advantages of the present invention can also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematically only and not to scale. It is noted in different figures, similar elements are provided with the same reference signs.

DETAILED DESCRIPTION OF EMBODIMENTS

Figure 1:
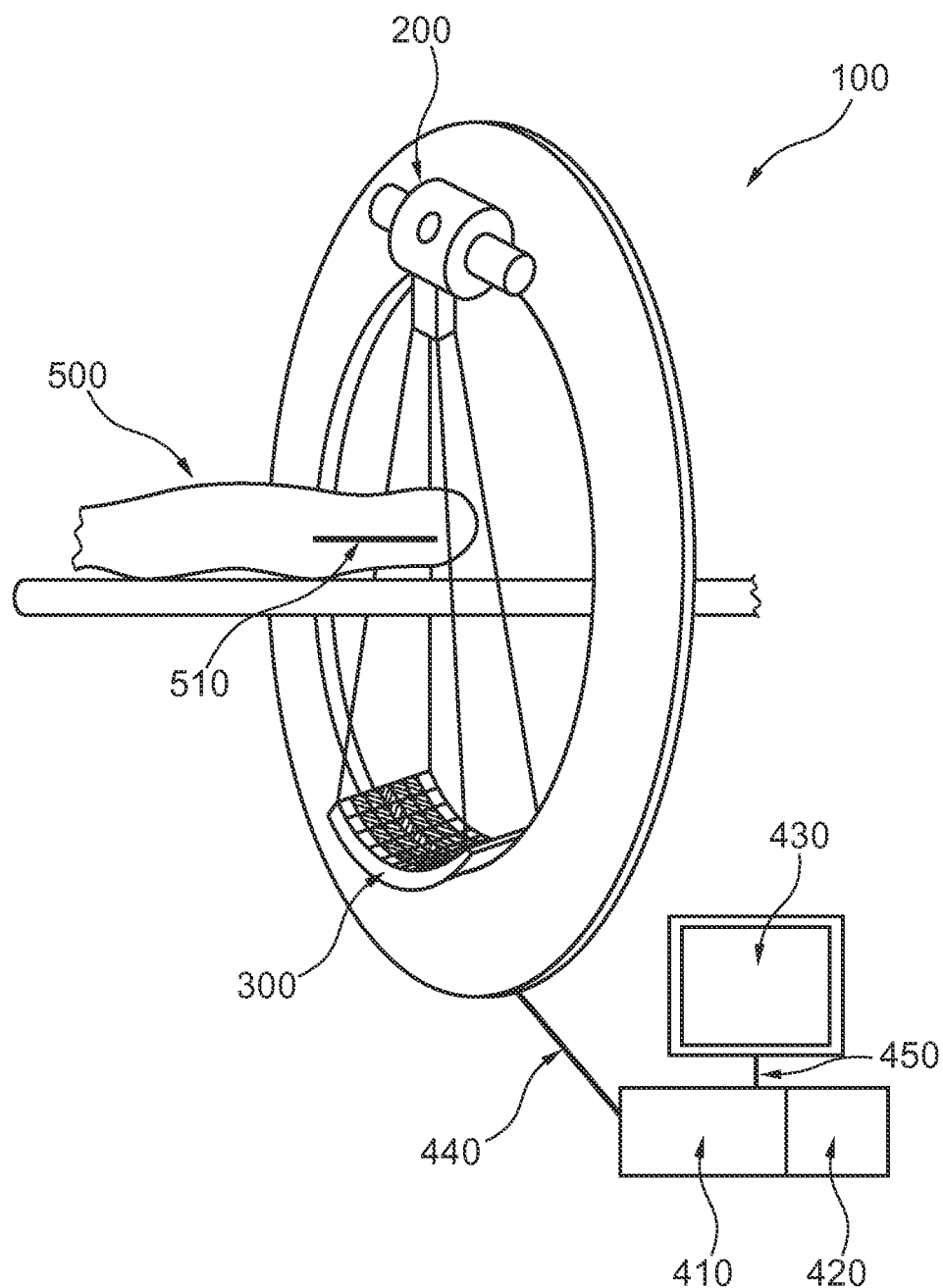
FIG. 1 shows a schematic illustration of a system according to an exemplary embodiment of the invention.

FIG. 1 shows a system 100 according to an exemplary embodiment of the invention. The system 100 comprises an imaging device having a radiation source 200 and a detector array 300 by means of which beams radiated from the radiation source, might be detected. Further, the system comprises a processing device 410 and a calculation device 420, which devices might be included in a single computing device having a working memory at which a corresponding program is stored. To visualize the result of the processing and calculating, a display device 430 like a monitor is provided in the system. The detector array 300 is connected to the processing device via a connection wire 440, and the processing device 410 is further connected to the display device 430 via another connection wire 450.

In FIG. 1 is also depict an object of interest 500 having a elongated element 510 as an inner structure.

While the system 100 is used, the radiation source 200, for example for X-ray radiation, emits a radiation beam which radiates through the object of interest 500 including the elongated element 510, and impinges at the detector array 300. The signals of the respective detectors, then, are transmitted to the processing unit which reconstructs a 3D volume image of the object of interest, which might be shown on the display device 430.

According to the invention, the processing unit 410 of the system 100 is adapted to determine the contour or cross section of the elongated element, i.e. the lines representing the walls of the elongated element. On the basis of the determined geometry of the elongated element, the calculation device 420 might calculate an asymmetry index. Finally, the reconstruction of the elongated element together with a visualization of the asymmetry index might be displayed on the monitor 430.

Figure 2:
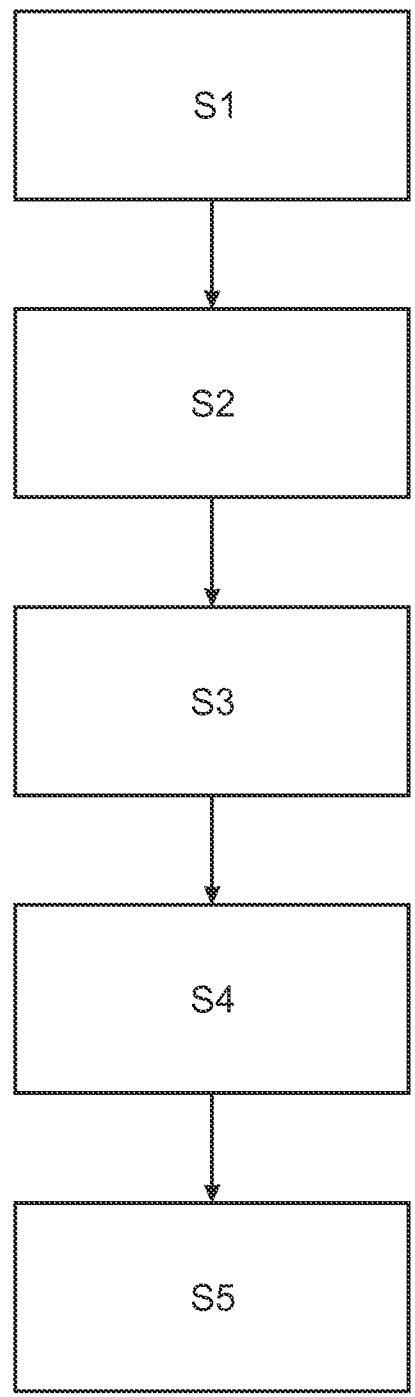
FIG. 2 shows successive steps of a method according to an exemplary embodiment of the invention.

FIG. 2 shows the steps of a method according to an exemplary embodiment of the invention. As denoted with respect to the different devices of the system 100, the method comprises the following steps (generally).

In step S1 a plurality of projections of the object of interest is generated, wherein the projections have different projection angles.

In step S2 geometrical aspects of the elongate element is determined in each of the projections, wherein the geometrical aspects might be the distance between opposite walls of the elongated element. Further, the maximal and minimal distances might be determined.

In step S3 an index is calculated on the basis of geometrical aspects determined in step S2. On the basis of for example the maximal and minimal diameters, an asymmetry index might be calculated.

In step S4 projections are indicated, having a desired value or range of value of the index. In this regard, it might be desired to know where the asymmetry of the elongated element is high or low. Thus, the desired value of the index depends on what the user of the system is investigating.

Finally, in step S5 the elongated element together with a visualization of the value of the index relative to the corresponding region of the elongated element is illustrated. Advantageously there might be an illustration on a monitor in which the index value is shown at the location at the elongated element, at which the geometric aspect valuated by the index, exists.

In the following, the method will be described with reference to figures showing exemplary illustration on a monitor.

Figure 3:
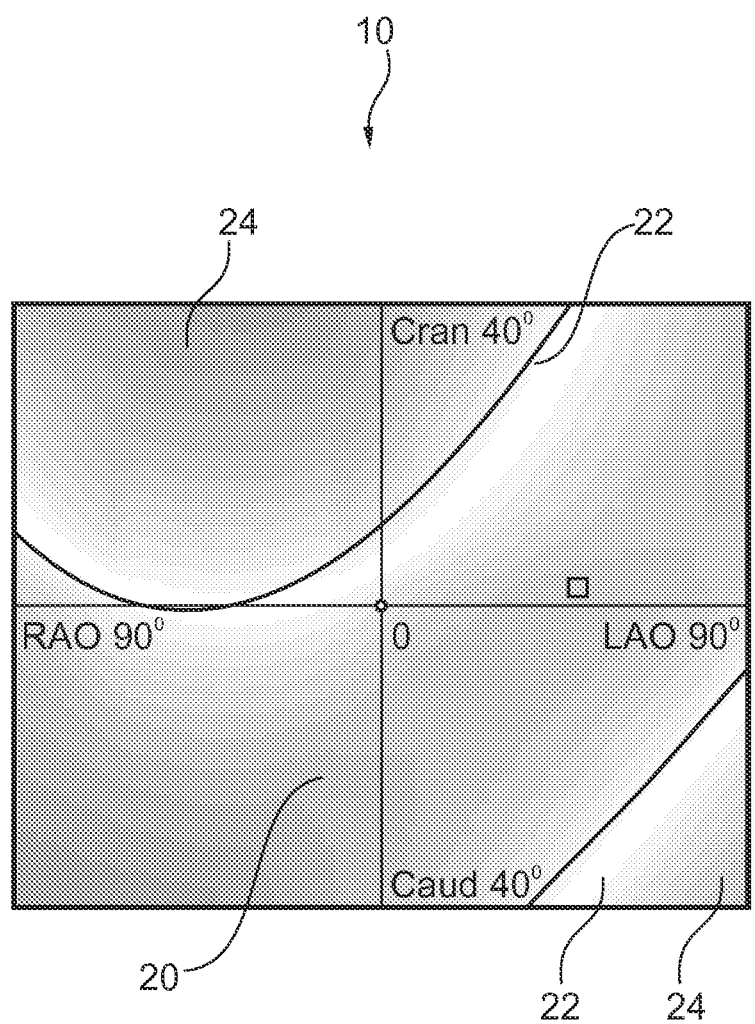
FIG. 3 shows a foreshortening optimal viewmap of a vessel segment of interest.

FIG. 3 depicts an exemplary foreshortening optimal viewmap 10. For each possible orientation of the X-ray system (from 90 degrees left anterior oblique (LAO) to 90 degrees right anterior oblique (RAO) and from 40 degrees caudal to 40 degrees cranial), the average foreshortening of a segment of an elongated element of interest is depicted. At this, the slightly curved middle region 20 represents a region of low foreshortening, the light strips 22 (here with a thin black line) represents regions of middle foreshortening, and the darker gray regions 24 represent regions of high foreshortening.

For a better visualization, this gray scale view might be colored. For example, region 20 might be green, the strips 22 might be yellow, and the regions 24 might be red, wherein the colors might change blurred from one to another region/strip.

Figure 4:
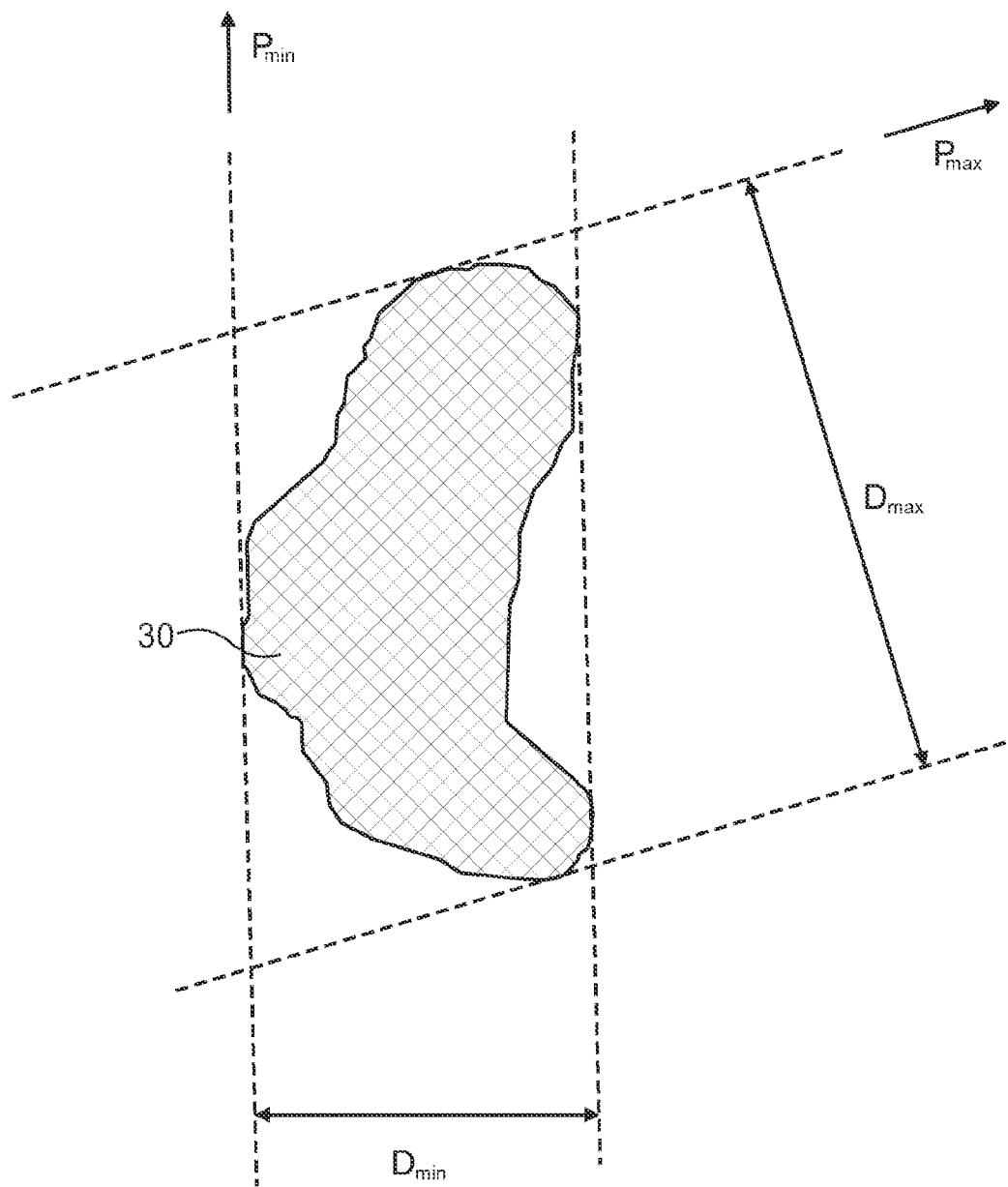
FIG. 4 shows a cross section of a vessel of interest.

FIG. 4 shows a cross section 30 of an exemplary elongated element in gray, perpendicular to center line of said element.

For a given cross sectional area there might be an X-ray projection direction $P_{max}$ that will result in the maximum diameter $D_{max}$ in the corresponding X-ray projection image, and a projection direction $P_{min}$ that will result in the minimum diameter $D_{min}$ in the X-ray projection image. For any projection $P_i$ the corresponding diameter $D_i$ can be determined. It should be noted that the projection directions might be advantageously in the plane of the cross-sectional area and therefore perpendicular to the centerline of the elongated element.

A maximum asymmetry index $A_{max}$ of the cross section 30 can be expressed for instance as $(D_{max}-D_{min})/D_{max}$, such that the asymmetry index $A_i$ becomes for any projection $P_i$, for example, $(D_{max}-D_i)/D_{max}$.

Figure 5:
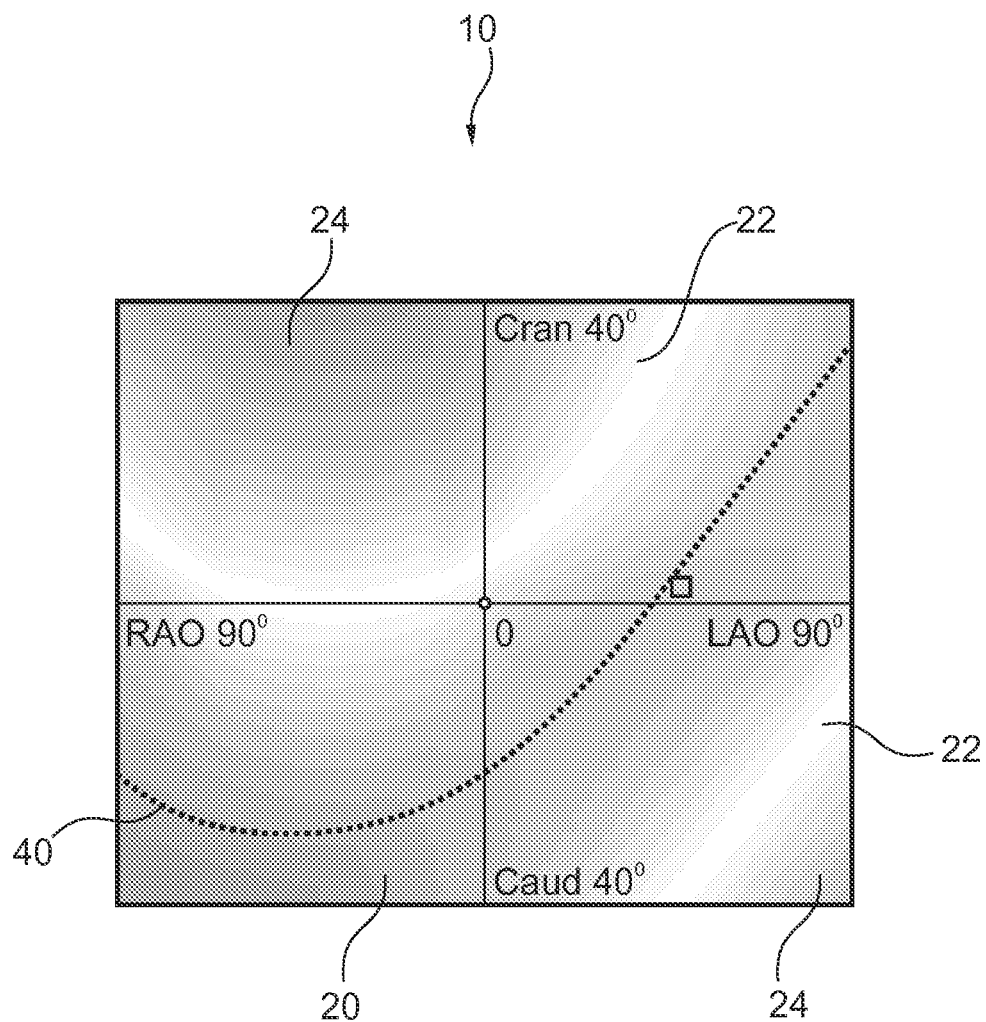
FIG. 5 shows an optimal viewmap with dotted line indicating several projection directions.

FIG. 5 shows an optimal viewmap 10 with dotted line 40 indicating all possible projection directions (in X-ray system coordinates) corresponding to a single cross section.

For a single cross section, all possible projection directions (perpendicular to the centerline of the vessel) might correspond to a line 40 in a map 10 of X-ray system orientations. For a single cross section the asymmetry index can be calculated as a function of all possible projection directions for that cross section, as described above.

Figure 6:
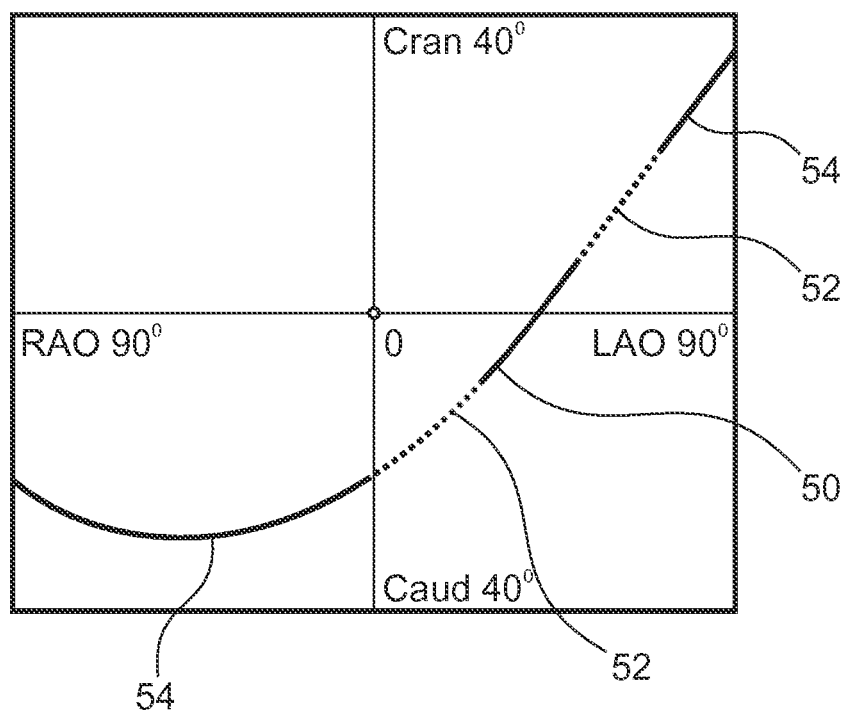
FIG. 6 shows a developing of values of an asymmetry index for a single cross section plotted against projection directions.

FIG. 6 shows only an asymmetry index for a single cross section plotted against projection directions in a map of system coordinates. Section 50 represents high asymmetry, sections 52 represent medium asymmetry and sections 54 represent low asymmetry.

Similar to the optimal viewmap the asymmetry index values can be color coded on a map of all possible system projection directions. This line can be color coded to display the asymmetry index value. Thus, the single sections might be illustrated in different colors, for example, section 50 in green, section 52 in orange, and section 54 in red.

Figure 7:
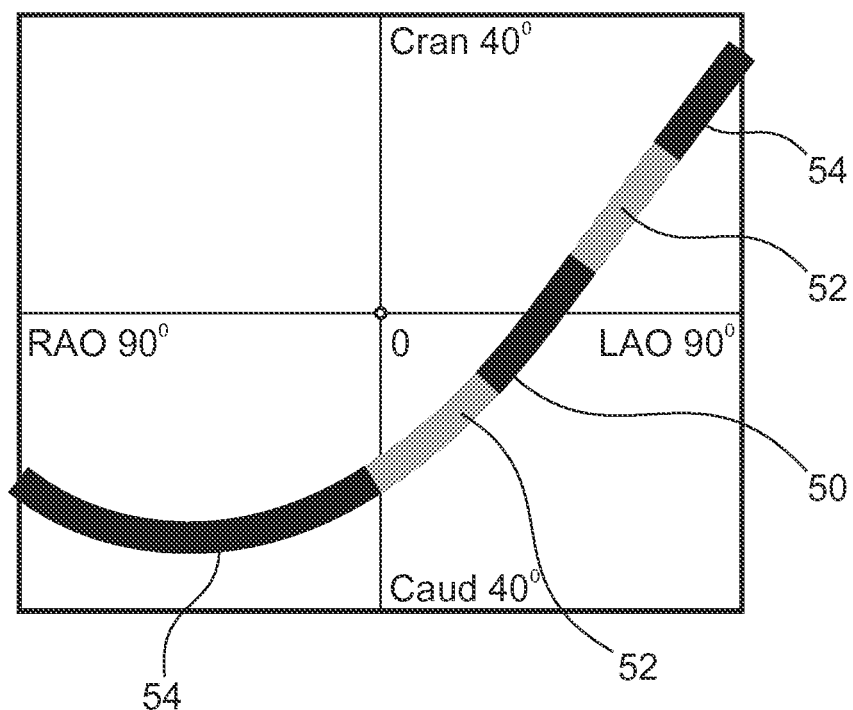
FIG. 7 shows another illustration of an asymmetry index for a vessel segment of interest.

FIG. 7 shows another asymmetry index for a segment of an elongated element like a vessel (consisting of multiple consecutive cross sections) plotted against projection directions in a map of system coordinates. Note that not the entire map is filled since only projection direction perpendicular to the cross sections in the selected vessel segment are evaluated. Section 50 illustrates high asymmetry, sections 52 illustrate medium asymmetry and sections 54 illustrate low asymmetry.

Since an elongated element narrowing is not restricted to a single cross section, a segment of said element needs to be assessed. By discretisation of the successive cross sections along an entire segment, the segment can be analyzed for asymmetry and the corresponding line sections for the individual cross sections depicted in a single plot. Since adjacent cross sections will differ only slightly in orientation (provided sufficient fine discretisation) this will result in continuous area in which values on the map are displayed.

Figure 8:
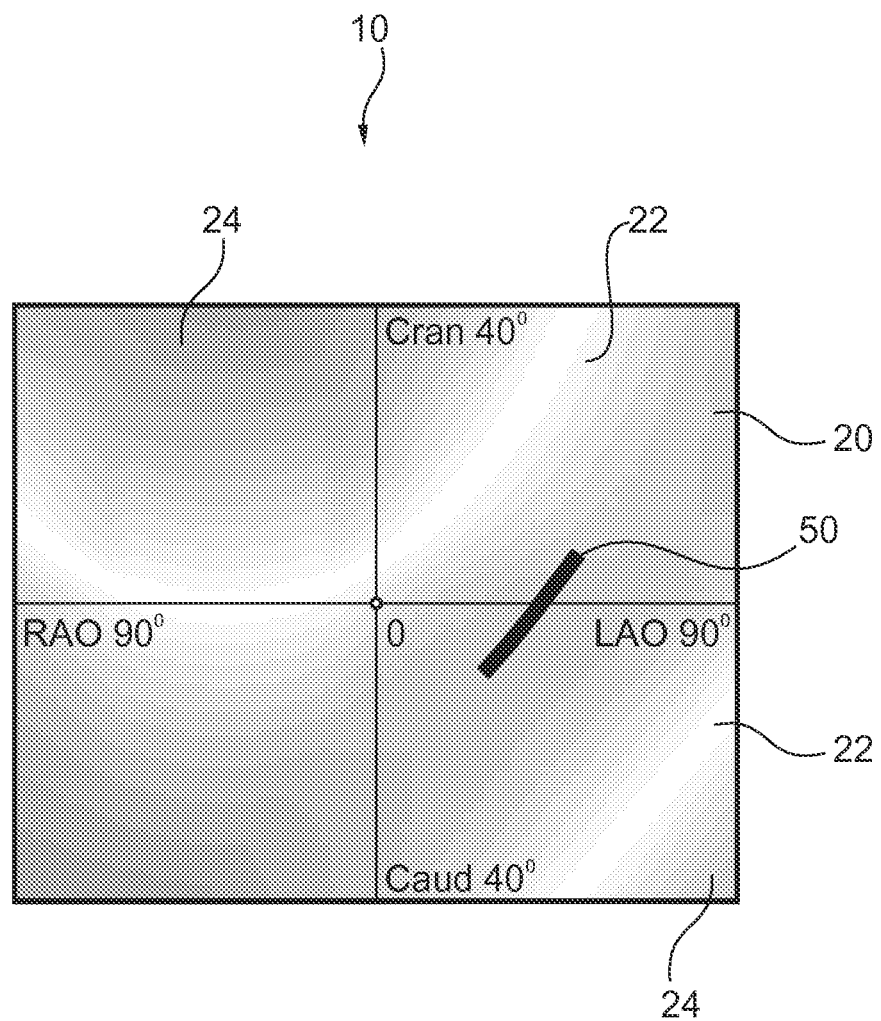
FIG. 8 shows an illustration of a foreshortening optimal viewmap fused with an asymmetry index having a desired value interval.

Finally, FIG. 8 shows a "foreshortening optimal viewmap" 10 fused together with a visualization 50 of a threshold of an index. The dark rectangle 50 represents a section of high asymmetry, region 20 stands for low foreshortening, strips 22 stand for medium foreshortening and regions 24 stand for high foreshortening.

Typically this method is only relevant for sufficiently asymmetric modifications or lesions and it therefore makes sense to only indicate areas where high asymmetry exists. This visualization may be fused with the existing "foreshortening optimal viewmap" resulting in a map that displays foreshortening but also indicates areas where the relevant minimum cross section can be seen (relevant for e.g. clinical application).

Alternatively to a gray scale or color coded presentation, only one maximum asymmetry index value of all evaluated cross sections may be plotted or its value can be given with the corresponding projection direction. Alternative calculations of an asymmetry index are possible but all based on the principle of using the cross sectional information to derive a projection direction of the X-ray system to determine the view that shows the minimum cross sectional area.

The plot of asymmetry index does not need to be restricted to angles that are feasible with the X-ray system (as in the examples) but may also be displayed for projection directions that are not physically feasible with the X-ray system (due to mechanic restrictions of the system).

While the invention has been illustrated and described in detail in the drawings and foregoing description, such illustration and description are to be considered illustrative or exemplary and. not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless

The invention claimed is:

1. A method of identifying modifications of an elongated element located in an object of interest, the method comprising the steps of:
    generating a plurality of projections of the object of interest, wherein the projections have different projection angles;
    determining geometrical aspects of the elongated element in each projection of the plurality of projections;
    calculating an index on a basis of the geometrical aspects of the elongated element in each projection of the plurality of projections; and
    indicating projections of the plurality of projections having a desired value or range of value of the index, wherein the indicated projections having the desired value or range of value of the index identify the modifications of the elongated element that comprise deformations of the elongated element, further wherein the desired value or range of value of the index represents a given asymmetry of a cross-section of a corresponding region of the elongated element.

2. The method of claim 1, wherein the geometrical aspects include a minimum diameter and a maximum diameter of the elongated element, measured perpendicular to a centre axis of the elongated element in each projection of the plurality of projections.

3. The method of claim 1, wherein the index comprises an asymmetry index, wherein the asymmetry index is normalized, so that a value of the asymmetry index is between 0 and 1 with higher values corresponding to more asymmetry and lower values corresponding to less asymmetry.

4. The method of claim 1, further comprising the step of illustrating the elongated element together with a visualization of a value of the index relative to a corresponding region of the elongated element.

5. A system for identifying modifications of an elongated element located in an object of interest, the system comprising:
    an imaging device adapted to generate a plurality of projections of the object of interest, wherein the projections have different projection angles;
    a processing device adapted to determine geometrical aspects of the elongated element in each projection of the plurality of projections; and
    a calculation device adapted to calculate an index on a basis of the geometrical aspects of the elongated element in each projection of the plurality of projections,
    wherein the processing device is further adapted to indicate projections of the plurality of projections having a desired value or range of value of the index, wherein the indicated projections having the desired value or range of value of the index identify the modifications of the elongated element that comprise deformations of the elongated element, further wherein the desired value or range of value of the index represents a given asymmetry of a cross-section of a corresponding region of the elongated element.

6. The system of claim 5, wherein the geometrical aspects include a minimum diameter and a maximum diameter of the elongated element, measured perpendicular to a centre axis of the elongated element in each projection of the plurality of projections.

7. The system of claim 5, wherein the index comprises an asymmetry index, wherein the asymmetry index is normalized, so that a value of the asymmetry index is between 0 and 1 with higher values corresponding to more asymmetry and lower values corresponding to less asymmetry.

8. The system of claim 5, further comprising a display device for illustrating the elongated element together with a visualization of a value of the index relative to a corresponding region of the elongated element.

9. A non-transitory computer-readable medium embodied with a computer program product adapted for execution by a processor for controlling a system for identifying modifications of an elongated element located in an object of interest, according to claim 5.

10. A non-transitory computer-readable medium, in which a computer program is stored, for controlling a system for identifying modifications of an elongated element located in an object of interest according to the method of claim 1.

* * * * *